United States Patent [19]

Kahne et al.

[11] Patent Number: 5,455,335

[45] Date of Patent: * Oct. 3, 1995

[54] PHARMACEUTICAL COMPOSITIONS AND METHODS OF TRANSPORTING COMPOUNDS ACROSS BIOLOGICAL MEMBRANE

[75] Inventors: Daniel E. Kahne; Suzanne W. Kahne, both of Princeton, N.J.

[73] Assignee: The Trustees of Princeton University, Princeton, N.J.

[*] Notice: The portion of the term of this patent subsequent to Aug. 16, 2011 has been disclaimed.

[21] Appl. No.: 224,862

[22] Filed: Apr. 8, 1994

Related U.S. Application Data

[63] Continuation of Ser. No. 806,985, Dec. 13, 1991, Pat. No. 5,338,837.

[51] Int. Cl.$^6$ .............................. C07J 9/00; C07J 41/00; A61K 31/56

[52] U.S. Cl. ............................. 536/5; 514/26; 514/178; 514/182; 514/885; 540/106; 424/451; 424/455; 424/456; 424/464

[58] Field of Search .................. 536/5; 540/106; 514/26, 178, 182, 885; 424/451, 455, 456, 464

[56] References Cited

U.S. PATENT DOCUMENTS

| | | | |
|---|---|---|---|
| 3,036,061 | 5/1962 | MacPhillamy et al. | 536/5 |
| 4,150,114 | 4/1979 | Smith | 424/59 |
| 4,260,736 | 4/1981 | Asano et al. | 536/5 |
| 4,360,663 | 11/1982 | Asano et al. | 536/5 |
| 4,900,555 | 2/1990 | Cheng et al. | 424/448 |
| 4,902,505 | 2/1990 | Pardridge et al. | 514/2 |
| 4,959,358 | 9/1990 | Carey et al. | 514/653 |
| 5,116,817 | 5/1992 | Anik | 514/15 |
| 5,144,017 | 9/1992 | LaBella et al. | 536/5 |
| 5,338,837 | 8/1994 | Kahne | 536/5 |

FOREIGN PATENT DOCUMENTS

| | | |
|---|---|---|
| 0101659 | 2/1984 | European Pat. Off. . |
| 0417725 | 3/1991 | European Pat. Off. . |
| 2007410 | 1/1970 | France . |
| 1527605 | 5/1975 | United Kingdom . |

OTHER PUBLICATIONS

Kahne, et al., *J. Am. Chem. Soc.* 111:6881 (1989).
Letsinger et al., *Proc. Natl. Acad. Sci.* USA 86:6553–6556 (Sep. 1989).
Brown et al., *Tetrahedron Letters* 29/38:4873–4876 (1988).
Dasgupta et al., *Carbohydrate Research* 177:c13–c17 (1988).
Ito et al., *Tetrahedron Letters* 1061–1064 (1988).
Andersson, et al., *Tetrahedron Letters* 3919–3922 (1986).
Hans Lonn, Carbohydrate Research 139:105–113 (1985).
Garegg, et al., *Carbohydrate Research* 116:162–165 (1983).
Nicolacu et al., *J. Am. Chem. Soc.*105:2430–2434 (1983).
Ferrier, et al., *Carbohydrate Research* 27:55–61 (1973).
Oehlke, J. *Pharmazie* (1979) 34 (H.7), 383–386.
Kramer, W. et al., *J. Bio. Chem.* (1992) 267(26), 18598–18604.
Gordon, G. S. et al., *Proc. Natl. Acad. Sci.* USA (1985) 82, 7419–7423.
Cheng, Y. et al., *J. Am. Chem. Soc.* (1992)114, 7319–7320.
Spigelman, M. K. et. al., *Neurosurgery* (1983)12(6), 606–612.
Malinowska, D. H. et al., *Proc. Natl. Acad. Sci.*USA (1981) 78(9), 5908–5912.
Oehlke; Chemical Abstracts 92:59167n (1980).
Oehlke; Chemical Abstracts 94:98644b (1981).
Riccio et al., Journal of Organic Chemistry 51:533–536 (1986).
Kramer et al., Chemical Abstracts 115:72019d (1991).

*Primary Examiner*—Ronald W. Griffin
*Attorney, Agent, or Firm*—Lowe, Price, Leblanc & Becker

[57] ABSTRACT

Novel glycosylated steroid derivatives for facilitating the transport of compounds across biological membranes are disclosed. A novel process for efficient synthesis of these glycosylated steroid derivatives, using activated glycosyl sulfoxide intermediates is also provided.

73 Claims, No Drawings

PHARMACEUTICAL COMPOSITIONS AND METHODS OF TRANSPORTING COMPOUNDS ACROSS BIOLOGICAL MEMBRANE

This invention was made with Government support under Grant No. N00014-91-J-1230, awarded by Office of Naval Research. The Government has certain rights in this invention.

This is a continuation of application Ser. No. 07/806,985, filed on Dec. 13, 1991, now U.S. Pat. No. 5,338,837.

BACKGROUND OF THE INVENTION

The present invention is generally directed to novel glycosylated steroid derivatives for facilitating the transport of molecules across biological membranes and the blood-brain barrier. The invention is further directed to a novel glycosylation process for the efficient synthesis of these glycosylated steroid derivatives.

The introduction of molecules of diagnostic, prophylactic, or therapeutic interest (termed herein "therapeutically-significant-molecules" or "therapeutically-significant-compounds") into cells requires traversal of one or more semi-permeable biological membranes. The basic structural unit of biological membranes is a phospholipid bilayer, in which are embedded proteins of various size and composition. The surfaces of the phospholipid bilayer, which project into the aqueous cellular environment, are formed by the hydrophilic heads of the phospholipids; the interior, by the fatty acyl hydrophobic tails. The membrane proteins may be involved in transport processes and also may serve as receptors in cellular regulatory mechanisms.

Natural mechanisms for traversal of biological membranes include passive diffusion, facilitated diffusion, active transport, receptor-mediated endocytosis and pinocytosis. Passive diffusion works best for small molecules which are lipid-soluble. However, biological membranes are essentially impermeable to most water-soluble molecules, such as nucleosides, amino acids, proteins, and other hydrophilic, therapeutically-significant molecules. Such molecules enter cells via some type of carrier-mediated transport system in which specific compounds facilitate traversal of the membrane. Natural carriers for facilitating traversal of the membrane are of limited utility, however, as such carriers will accept substrates of only a predetermined molecular configuration.

Specific strategies also have been proposed for introducing molecules, particularly oligonucleotides, into the cell nucleus. Among the techniques reported are utilization of HIV Tat protein-drug conjugates [WO 91/09958] and utilization of oligonucleotide-cholesterol conjugates [Letsinger R.L. et al. "Cholesteryl-conjugated oligonucleotides: Synthesis, properties, and activity as inhibitors of replication of human immunodeficiency virus in cell culture." *Proc. Natl. Acad. Sci. USA* 86: 6553–6556 (September 1989); Stein C. A. et al. "Mode of Action of 5'-Linked Cholesteryl Phosphorothioate Oligodeoxynucleotides in Inhibiting Syncytia Formation and Infection by HIV-1 and HIV-2 in Vitro." *Biochemistry* 30: 2439–2444 (1991)].

Targeting molecules to the brain requires traversal of the blood-brain barrier—a capillary-including system, with unique morphological characteristics, which acts as a systemwide cellular membrane separating the brain interstitial space from the blood. Like biological membranes, the blood-brain barrier is relatively impermeable to many hydrophilic, therapeutically-significant-compounds. Among the strategies which have been developed for targeting compounds to the brain are direct delivery by invasive procedures, intra-arterial infusion of hypertonic substances, and conversion of hydrophilic compounds to lipid-soluble entities. Recent attempts at facilitated transport, as described in U.S. Pat. No. 4,902,505, involve coupling a hydrophilic peptide of interest to a peptide carrier which, by itself, is capable of traversing the barrier via receptor-mediated transcytosis.

The carrier compounds of the present invention are novel glycosylated steroid derivatives, soluble in both aqueous and membrane-like environments. Unlike previously-known carriers, the compounds of the present invention may be used to facilitate the transport of a wide variety of molecules, particularly in vivo.

Prior to the present invention, no method existed for synthesizing all of the glycosylated steroid derivatives of the present invention. Many glycosylation reactions using thioglycosides have been reported. [Ferrier R. J. et al. "A Potentially Versatile Synthesis of Glycosides." *Carbohydrate Research* 27: 55–61 (1973); Garegg P. J. et al. "A reinvestigation of glycosidation reactions using 1-thioglycosides as glycosyl donors and thiophilic cations as promoters." *Carbohydrate Research* 116: 162–5 (1983); Nicolaou K. C. et al. "A Mild and General Method for the Synthesis of O-Glycosides." *J Am Chem Soc* 105: 2430–2434 (1983); Lonn H. "Synthesis of a tri- and a hepta-saccharide which contain α-L-fucopyranosyl groups and are part of the complex type of carbohydrate moiety of glycoproteins." *Carbohydrate Research* 139: 105–113 (1985); Andersson F. et al. "Synthesis of 1,2-cis-linked glycosides using dimethyl(methylthio)sulfonium triflate as promoter and thioglycosides as glycosyl donors." *Tetrahedron Letters* pp. 3919–3922 (1986); Brown D. S. et al. "Preparation of cyclic ether acetals from 2-benzenesulphonyl derivatives: a new mild glycosidation procedure." *Tetrahedron Letters* 29/38: 4873–4876 (1988); Ito Y et al. "Benzeneselenenyl triflate as a promoter of thioglycosides: a new method for O-glycosylation using thioglycosides." *Tetrahedron Letters* pp. 1061–4 (1988); Dasgupta F. et al. "Alkyl sulfonyl triflate as activator in the thioglycoside-mediated formation of β-glycosidic linkages during oligosaccharide synthesis." *Carbohydrate Research* 177: c13–c17 (1988)]. However, none of these reported methods teach the use of a glycosyl sulfoxide as a glycosylating agent.

Utilization of an activated glycosyl sulfoxide intermediate in a process for glycosylating steroids, previously has been reported by the inventor in *J. Am. Chem. Soc.* 111: 6881–2 (1989), the content of which is hereby incorporated by reference. However, the reported method represents only preliminary results on the glycosylation of steroids of the Formula (I). More specifically, further experimentation in the series has revealed unique reaction conditions which are necessary to achieve the efficient and stereo-selective synthesis of glycosylated compounds of the Formula (I). The reaction solvent used plays a critical role in the stereoselectivity of glycosylation. Using a nonpolar, aprotic solvent increases selectivity for alpha (α) glycosidic bond formation while the use of a polar, aprotic solvent such as propionitrite increases selectivity for beta (β) glycosidic bond formation. The type of sulfoxide used in the glycosylation reaction also affects the stereoselectivity of the reaction. For example, it is vital to use the para-methoxy phenyl sulfoxide as the leaving group in the novel process described herein to obtain beta (β) selectivity in the glycosidic bond formation. The yield of the glycosylation reaction yielding alpha (α) or beta (β) glycosidic linkages may be increased by the use of less than one equivalent of triflic anhydride in the glycosylation process.

Finally, the protecting groups on the glycosyl donor also have an impact on the stereochemical course of the glycosylation reaction. When the protecting group used on the glycosyl donor is pivaloyl, only beta (β) glycosidic bonds are formed in the glycosylation process, regardless of whether an aprotic, non-polar solvent or an aprotic, polar solvent is used for the reaction. The above factors taken together indicate that one skilled in the art could not have practiced the invention without the detailed further experimentation provided herein.

SUMMARY OF THE INVENTION

The present invention is generally directed to novel glycosylated steroid derivatives and the process for obtaining said derivatives which have been found to be soluble in both aqueous and membrane-like environments. Their solubility properties permit the glycosylated steroid derivatives to facilitate the transport of other molecules across biological membranes and the blood brain barrier.

Of particular interest are the steroid derivatives of the general formula (I)

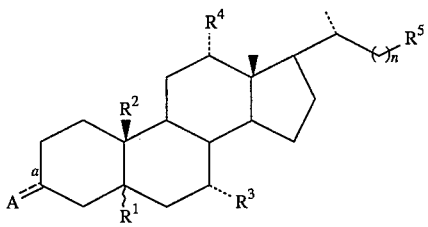

wherein

A is O, OH, $OR^6$, $NR^7R^8$, $N_3$, $NHCOR^7$, OCOAr

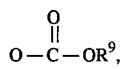

$OCOR^9$, $NHCH_2C_6H_5$

Ar is phenyl or phenyl substituted with 1–3 groups selected from the group consisting of halogen, $C_1$–$C_{12}$ alkyl or $C_1$–$C_3$ alkoxy;

a is a single bond in the alpha or beta configuration with the proviso that when A=O, a is a double bond;

$R^1$ is H which is cis or trans to $R^2$;

$R^2$ is $CH_3$;

$R^3$ is H, OH or $OR^6$;

$R^4$ is H, OH or $OR^6$;

$R^5$ is $CO_2R^{10}$, $CH_2OR^9$, $CONH_2$, $CONHR^7$, $CONR^7R^8$,

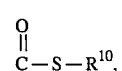

$CH_2S(O)_p$—S—$R^{10}$ $CH_2NH_2$, $CH_2NHR^7$, $CH_2NR^7R^8$, $CH_2$—S(O)$_p$—S—$R^{10}$;

$R^6$ is a monosaccharide where the glycosidic linkage at the anomeric carbon atom in said monosaccharide is alpha or beta or is an oligosaccharide of 2–10 monosaccharides where the glycosidic linkage at any of the anomeric carbon atoms in each monosaccharide residue of the oligosaccharide is independently alpha or beta;

$R^7$ and $R^8$, independently are H, $C_1$–$C_4$ alkyl, $C_3$–$C_7$ cycloalkyl, $C_4$–$C_{10}$ alkylcycloalkyl, phenyl, benzyl, or, taken together are $(CH_2)_f$, where f=3–6;

$R^9$ is H or, $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

Monosaccharide is a protected or deprotected hexose or deoxyhexose comprising D-allose, D-altrose, D-glucose, D-mannose, D-gulose, D-idose, D-galactose, D-talose or a protected or deprotected furanose or deoxyfuranose selected from the group consisting of D-ribose, D-arabinose, D-xylose or D-lyxose where said protecting groups for the hydroxy groups of said hexoses or furanoses are selected from the group consisting of benzyl, pivaloyl, trimethylsilyl, tert-butyldimethylsilyl, tert-butyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl and allyl;

p is 0, 1 or 2;

n is 0, 1 or 2;

or a pharmaceutically suitable salt thereof.

Also provided are methods for transporting any therapeutically-significant-compound, linked to compounds of Formula (I) through any of $R^5$, which is to be introduced into the cell or the nucleus of the cell or across the blood-brain barrier where said therapeutically-significant compound includes, but is not limited to, peptides or proteins, such as regulatory factors, enzymes, antibodies and toxins; nucleotides, nucleosides and nucleic acids; saccharides; and wherein the A and B rings of the steroidal residue of said compounds of Formula (I) may be cis or trans to one another; and the O glycosidic linkage at C-7 and C-12 may be in the alpha or beta configuration, each independently of the other.

Also provided are pharmaceutical compositions containing an effective amount of a compound of Formula (I) and a suitable pharmaceutical carrier.

The invention is further directed to a novel process (Scheme I) for the efficient synthesis of glycosylated steroid derivatives of the Formula (I) which comprise: (a) reacting a protected glycoside, which is prepared by standard methods for conversion of a sugar well known to those of ordinary skill in the art, where the oxygen atoms at all positions of the sugar except the anomeric position are protected with the same or different groups, with (b) an —S—R entity under standard conditions, where R is $C_1$–$C_{10}$ alkyl, pyrindyl, furyl, thienyl, pyridyl, phenyl or phenyl substituted with 1–3 groups selected from the group comprising halogen, $C_1$–$C_3$ alkyl, $NO_2$, $C_1$–$C_3$ alkoxy, to yield a protected thio-glycoside which is further reacted with (c) meta-chloroperoxybenzoic acid to yield the corresponding sulfoxide derivative and (d) converted to an activated glycosylating agent intermediate using a triflate-containing compound, such as triflic anhydride, methyl triflate or trimethylsilyl triflate and contacting said activated glycosylating agent with (e) asteroid (in which any oxygens which are not to be glycosylated have been protected by standard methods) in the presence of 2,6-di-tert-butyl- 4-methylpyridine in toluene, for formation of alpha, alpha glycosidic linkages, or in propionitrile, for the formation of beta, beta glycosidic linkages thereby yielding a protected glycosylated steroid which is then deprotected by removing the protecting groups by (f) standard procedures to yield glycosylated steroids of the Formula (I). The oxygen-protecting groups utilized may be either electron-withdrawing groups such as esters; or electron-donating groups, such as ethers, including alkyl, silyl, phenyl or benzyl ethers. However, if a pivaloyl ester is the protecting group used, the resulting glycosidic linkage that is formed is always β,β regardless of the solvent used for the reaction. The resulting compounds of the invention may be characterized by proton NMR, $C^{13}$—NMR, high resolution mass spectroscopy, X-ray crystallography and thin layer chromatography.

Preferred for their ability to permeabilize biological membranes are those compounds of Formula (I) where:

A is OH,

$OCOC_6H_5$, $OCOC_6H_4$—pOMe, $NH_2$;

a is a single bond;

$R^3$ is $OR^6$;

$R^4$ is $OR^6$;

$R^5$ is $CO_2R^{10}$, $CONR^7R^8$;

$R^6$ is a monosaccharide where the glycosidic linkage at the anomeric carbon atom in said monosaccharide is alpha or beta;

$R^{10}$ is H or $C_1$—$C_{10}$ alkyl;

Monosaccharide is a protected or deprotected hexose such as D-glucose where the protecting groups are benzyl or pivaloyl.

Specifically preferred for their ability to permeabilize biological membranes are:

(a) 3α-O-Benzoyl-trans-5,10-bis-β,β-7,12-glucosyl cholic acid methyl ester;

(b) 3α-Hydroxy-cis-5,10-bis-α,α-7,12-glucosyl cholic acid;

(c) 3α-Hydroxy-cis-5,10-bis-α,α-7,12-glucosyl cholic acid methyl ester;

(d) 3α-Hydroxy-cis-5,10-bis-α,α-7,12-glucosyl- 25-tryptophanyl cholic acid;

(e) 3α-Ethylcarbonate-cis-5,10-bis-α,α-7,12-glucosyl cholic acid methyl ester;

(f) 3α-O-Benzoyl-cis-5,10-bis-α,α-7,12-glucosyl cholic acid methyl ester;

(g) 3α-O-p-Methoxybenzoyl-cis-5,10-bis-α,α-7,12-glucosyl cholic acid methyl ester;

(h) 3α-O-Benzoyl-cis-5,10-bis-α,α-7,12-glucosyl cholic acid methyl ester;

(i) 3α-Hydroxy-cis-5,10-bis-α,α-7,12-glucosyl cholic acid;

(j) 3α-O-Benzoyl-trans-5,10-bis-α,α-7,12-glucosyl cholic acid methyl ester;

(k) 3α-Hydroxy-trans-5,10-bis-α,α-7,12 glucosyl cholic acid.

DETAILED DESCRIPTION OF THE INVENTION

The compounds of this invention are useful in permeabilizing biological membranes, thereby assisting membrane transversal of therapeutically significant compounds and facilitating the transport of hydrophilic compounds not attached covalently to the steroid. Alternatively, the compound of interest is conjugated to the glycosylated steroid, i.e., $R^5$ is linked to a therapeutically significant compound, for traversal of the cellular and/or nuclear membrane. The introduction of molecules of diagnostic, prophylactic, or therapeutic interest into cells requires the transversal of one or more semi-permeable biological membranes.

The therapeutic applications for the compounds of the present invention are practically limitless. Membrane permeable therapeutic agents could be used in the treatment of a wide variety of illnesses such as AIDS and other chronic viral infections, cancer, bacterial and fungal infections, and metabolic diseases such as lupus, diabetes and rheumatoid arthritis.

Using the novel technology described herein, the compounds of Formula (I) are soluble in water and in membrane-like environments, enabling them to facilitate the transport of small hydrophilic molecules across membrane-like barriers. The compounds of the instant invention are unlike any other transmembrane carriers known to those of ordinary skill in the art. Additionally, the compounds of the present invention facilitate the transport of protons or other ions such as $Ca^{+2}$, $Na^+$ or $K^+$ across biological membranes indicating their use as potential antifungal or antibiotic agents.

Alternatively, the glycosylated steroid/therapeutically—significant compound conjugate can be used in vivo, as a component of a pharmaceutical composition in a manner similar to more conventional therapeutic agents. Administration of the conjugate to an individual with a chronic viral infection may inactivate the virus or the conjugate may contain an antisense oligonucleotide sequence which is inhibitory to viral gene or oncogene activity. For the individual with a genetic defect, the therapeutically-significant compound can be a protein which supplements a missing or defective protein.

Alternatively, the glycosylated steroid/therapeutically-significant compound conjugate may be administered as a pharmaceutical composition via a variety of routes, including subcutaneous, intravenous, intramuscular, intrasternal, intranasal and intracranial injection or infusion. The pharmaceutical composition also maybe administered topically or via inhalation.

SYNTHESIS

The compounds of Formula (I) can be prepared according to the process shown in Scheme I.

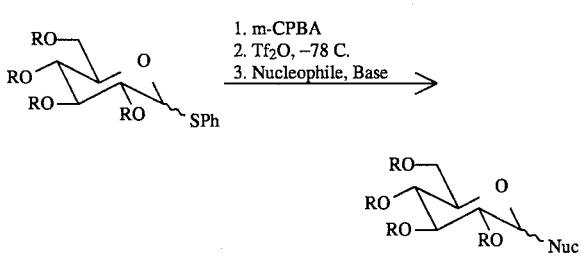

SCHEME I

A protected thioglycoside is oxidized with m-chloroperoxybenzoic acid under standard conditions to yield the corresponding sulfoxide. Triflic anhydride (Aldrich) is then added to a solution of the protected glycosyl sulfoxide in toluene at −78° C. followed by the addition of an acid scavenger such as 2,6-di-tert-butyl-4-methyl pyridine (Aldrich Chemical Co.) in toluene and the nucleophile dissolved in toluene at −78° C. After stirring for 15–30 minutes, the reaction was removed from the cold bath and stirred for an additional 10 minutes and quenched by pouring the mixture into aqueous sodium bicarbonate and the protected adduct was isolated by chromatography. Deprotection of the adduct under standard conditions yields compounds of the Formula (I). The appropriate thioglycoside is obtained via standard protection of a selected sugar followed by thioglycoside formation according to methods described above. Via this method, bis-glycosylation of a steroid derivative of the Formula (I) where $R^3$ and $R^4$ are OH selectively produces α,α glycosidic linkages with the glycosyl donor, except where the protecting group used is pivaloyl, in which case only β,β glycosidic linkages are formed regardless of the solvent used for the reaction.

Alternatively, the protected glycosyl sulfoxide, nucleophile and pyridine base are dissolved in propionitrile at −78° C., followed by the addition of triflic anhydride at −78° C. and the product is isolated as described above. Via this method, glycosylation of a steroid derivative of the Formula (I) where $R^3$ and $R^4$ are OH selectively produces β,β glycosidic linkages with the glycosyl donor. It is vital to use the p-methoxy phenyl sulfoxide as the leaving group in the above process to obtain the β,β selectivity in the glycosylation.

The compounds of this invention and their preparation are illustrated further in the following examples. All temperatures are in degrees Centigrade and parts and percentages by weight. In these Examples, unless otherwise indicated, the reactions were performed under an atmosphere of dry argon; "isolation by extraction" refers to the liquid-liquid extraction of a water containing mixture with an indicated solvent, followed by drying the organic phase over sodium sulfate, filtering, and evaporating the solvent under reduced pressure; chromatography refers to the method of medium pressure column chromatography described by W. C. Still, et al., *Journal of Organic Chem.*, 43: 2923 (1978).

EXAMPLE 1

Part A: Perbenzylated-3α-Ethylcarbonate-cis-5,10-bis-α,α-glucosyl cholic acid methyl ester.

A 100 ml round bottom flask containing a Teflon® stir bar is flame dried and cooled to −78° C. (acetone/dry ice bath) under argon. 2,3,4,6-tetra-O-benzyl glucose sulfoxide (2.97 g, 4.57 mmol, 4.0 eq.), $C_3$ ethylcarbonate cholic acid (0.563 g, 1.14 mmol, 1.0 eq.) and 2,6-di-tert-butyl-4-methylpyridine (0.936 g, 4.57 mmol, 4.0 eq.) are each dried by azeotroping each separately three times with toluene (15.0 ml). Triflic anhydride (824 µl, 4.57 mmol, 4.0 eq.) is added to the glycosyl sulfoxide dissolved in toluene (5.0 ml) at −78° C. To this mixture is then added the pyridine base in toluene (5.0 ml). After five minutes, the cholic acid derivative, dissolved in methylene chloride (1.0 ml) and toluene (5.0 ml). is added. The reaction is allowed to stir at −78° C. for thirty minutes and then removed from the dry ice bath. After ten minutes, the reaction is quenched by the addition of saturated sodium bicarbonate and the product was isolated by extraction with methylene chloride and purified by flash chromatography on silica gel to provide the title compound (60%) as an oil, $R_F$=0.3 (20% ether/$CH_2Cl_2$).

Part B: 3α-Ethylcarbonate-cis-5,10-bis-α,α-glucosyl cholic acid methyl ester.

Palladium hydroxide (0.030 g, 15% by weight) is added to a mixture of the product of Part A (0.220 g, 0.014 mmol, 1.0 eq.) dissolved in benzene (4.0 ml) and methanol (32.0 ml) at room temperature. The mixture is hydrogenated at 50 psi for 48 hours. The product is filtered through Celite® (diatomaceous silica, Johns-Manville Corp.) under nitrogen. The solvent was evaporated and the oil was flash chromatographed with 10% methanol/methylene chloride. To remove the silica gel that dissolves under elution conditions, the product is run through on a reverse phase LH-20 column using methanol as an eluent. The solvent is evaporated to yield the title compound (65%) as a white powder, $R_F$=0.3 (15% MeOH/$CH_2Cl_2$), NMR ($CDCl_3$ 500 MHz) δ:5.04 (m, 1H, anomeric β-H̲), 4.82 (m, 1H, anomeric β-H̲).

EXAMPLE 2

3α-Benzoyl-cis-5,10-bis-β,β-glucosyl cholic acid methyl ester.

2,3,4,6-Tetra-O-benzyl p-methoxy glucose sulfoxide (1.012 g, 1.45 mmol, 4.0 eq.), C3-O-benzoyl cholic acid methylester (0.191 g, 0.364 mmol, 1.0 eq.) and 2,6-di-tert-butyl-4 methyl pyridine (0.179 g, 0.874 mmol, 2.4 eq.) are azeotroped together three times from toluene (20 ml). After removing the toluene under reduced pressure for the last time, the mixture is dissolved in freshly distilled propionitrile and cooled under argon in a dry ice/acetone bath at −78° C. Triflic anhydride (244 µl, 1.45 mmol, 4.0 eq.) is added and the reaction mixture is stirred at −78° C. for 40 minutes. The reaction vessel is removed from the ice bath and stirred for an additional 10 minutes. The reaction is quenched by pouring it into saturated sodium bicarbonate and the product is isolated by extraction with methylene chloride and purified by flash chromatography on silica gel. Catalytic hydrogenation to remove the benzyl protecting groups is accomplished as described above to yield the title compound (60%) as an oil, $R_F$= 0.3 (15% MeOH/$CH_2Cl_2$), NMR ($CDCl_3$ 500 MHz) δ:4.36 (d, 1H, J=7.92 Hz, anomeric α-H̲), 4.37 (d, 1H, J=7.92 Hz, anomeric α-H̲).

The compounds of Example 1 and 2 and compounds which were prepared or could be prepared following procedures analogous to those outlined above are shown in Table I.

TABLE I

| EX | A | a* | R¹* | R² | R³** | R⁴** | R⁵ | n |
|----|---|----|----|----|------|------|----|---|
| 1[b] | O=C(OCOEt) | s (α) | H (β) | $CH_3$ | O-glucose (α) | O-glucose (α) | $CO_2Me$ | 2 |
| 2[c] | OCOPh | s (α) | H (β) | $CH_3$ | O-glucose (β) | O-glucose (β) | $CO_2Me$ | 2 |
| 3[d] | OH | s (α) | H (β) | $CH_3$ | O-glucose (α) | O-glucose (α) | $CO_2H$ | 2 |
| 4[e] | OH | s (α) | H (β) | $CH_3$ | O-glucose (α) | O-glucose (α) | $CO_2Me$ | 2 |
| 5[f] | OH | s (α) | H (β) | $CH_3$ | O-glucose (α) | O-glucose (α) | CONH—Tryptophan | 2 |
| 6 | O=C(OCOEt) | s (α) | H (β) | $CH_3$ | O-glucose (α) | O-glucose (α) | $CO_2Me$ | 2 |
| 7[g] | OCOPh | s (α) | H (β) | $CH_3$ | O-glucose (α) | O-glucose (α) | $CO_2Me$ | 2 |
| 8[h] | OCOPh—OMe | s (α) | H (β) | $CH_3$ | O-glucose (α) | O-glucose (α) | $CO_2Me$ | 2 |
| 9[i] | OCOPh | s (α) | H (α) | $CH_3$ | O-glucose (β) | O-glucose (β) | $CO_2Me$ | 2 |
| 10[j] | OH | s (α) | H (β) | $CH_3$ | O-glucose (β) | O-glucose (β) | $CO_2H$ | 2 |
| 11[k] | OCOPh | s (α) | H (α) | $CH_3$ | O-glucose (α) | O-glucose (α) | $CO_2Me$ | 2 |
| 12 | OH | s (α) | H (α) | $CH_3$ | O-glucose (α) | O-glucose (α) | $CO_2H$ | 2 |
| 13[l] | OH | s (α) | H (α) | $CH_3$ | O-glucose (β) | O-glucose (β) | $CO_2H$ | 2 |
| 14 | $NH_2$ | s (α) | H (β) | $CH_3$ | O-glucose (α) | O-glucose (α) | $CO_2H$ | 2 |
| 15 | O=C(OCOEt) | s (α) | H (β) | $CH_3$ | O-glucose (β) | O-glucose (β) | $CO_2Me$ | 2 |
| 16 | O=C(OCOEt) | s (α) | H (α) | $CH_3$ | O-glucose (β) | O-glucose (Θ) | $CO_2Me$ | 2 |
| 17 | O | d | H (α) | $CH_3$ | O-glucose (α) | O-glucose (α) | $CO_2H$ | 2 |
| 18 | O | d | H (α) | $CH_3$ | O-glucose (β) | O-glucose (β) | $CO_2H$ | 2 |
| 19 | O | d | H (β) | $CH_3$ | O-glucose (α) | O-glucose (α) | $CO_2H$ | 2 |
| 20 | O | d | H (β) | $CH_3$ | O-glucose (β) | O-glucose (β) | $CO_2H$ | 2 |
| 21 | O | d | H (α) | $CH_3$ | O-glucose (α) | O-glucose (α) | $CO_2Me$ | 2 |
| 22 | O | d | H (α) | $CH_3$ | O-glucose (β) | O-glucose (β) | $CO_2Me$ | 2 |
| 23 | O | d | H (β) | $CH_3$ | O-glucose (α) | O-glucose (α) | $CO_2Me$ | 2 |
| 24 | O | d | H (β) | $CH_3$ | O-glucose (β) | O-glucose (β) | $CO_2Me$ | 2 |
| 25 | $OCH_2Ph$ | s (α) | H (α) | $CH_3$ | O-glucose (α) | O-glucose (α) | $CO_2H$ | 2 |
| 26 | $OCH_2Ph$ | s (α) | H (α) | $CH_3$ | O-glucose (β) | O-glucose (β) | $CO_2H$ | 2 |
| 27 | $OCH_2Ph$ | s (α) | H (β) | $CH_3$ | O-glucose (α) | O-glucose (α) | $CO_2H$ | 2 |
| 28 | $OCH_2Ph$ | s (α) | H (β) | $CH_3$ | O-glucose (β) | O-glucose (β) | $CO_2H$ | 2 |
| 29 | $OCH_2Ph$ | s (α) | H (α) | $CH_3$ | O-glucose (α) | O-glucose (α) | $CO2Me$ | 2 |
| 30 | $OCH_2Ph$ | s (α) | H (α) | $CH_3$ | O-glucose (β) | O-glucose (β) | $CO_2Me$ | 2 |
| 31 | $OCH_3Ph$ | s (α) | H (β) | $CH_3$ | O-glucose (α) | O-glucose (α) | $CO_2Me$ | 2 |
| 32 | $OCH_3Ph$ | s (α) | H (β) | $CH_3$ | O-glucose (β) | O-glucose (β) | $CO_2Me$ | 2 |
| 33 | O=C(OCOEt) | s (α) | H (α) | $CH_3$ | O-galactose (α) | O-galactose (α) | $CO_2H$ | 2 |
| 34 | O=C(OCOEt) | s (α) | H (α) | $CH_3$ | O-galactose (β) | O-galactose (β) | $CO_2H$ | 2 |
| 35 | O=C(OCOEt) | s (α) | H (β) | $CH_3$ | O-galactose (α) | O-galactose (α) | $CO_2H$ | 2 |
| 36 | O=C(OCOEt) | s (α) | H (β) | $CH_3$ | O-galactose (β) | O-galactose (β) | $CO_2H$ | 2 |
| 37 | O=C(OCOEt) | s (α) | H (α) | $CH_3$ | O-galactose (α) | O-galactose (α) | $CO_2Me$ | 2 |

TABLE I-continued

| EX | A | a* | R¹* | R² | R³** | R⁴** | R⁵ | n |
|----|---|-----|------|-----|-------|-------|------|---|
| 38 | O‖OCOEt | s (α) | H (α) | CH₃ | O-galactose (β) | O-galactose (β) | CO₂Me | 2 |
| 39 | O‖OCOEt | s (α) | H (β) | CH₃ | O-galactose (α) | O-galactose (α) | CO₂Me | 2 |
| 40 | O‖OCOEt | s (α) | H (β) | CH₃ | O-galactose (β) | O-galactose (β) | CO₂Me | 2 |
| 41 | OCOPh | s (α) | H (α) | CH₃ | O-ribose (α) | O-ribose (α) | CO₂H | 2 |
| 42 | OCOPh | s (α) | H (α) | CH₃ | O-ribose (β) | O-ribose (β) | CO₂H | 2 |
| 43 | OCOPh | s (α) | H (β) | CH₃ | O-ribose (α) | O-ribose (α) | CO₂H | 2 |
| 44 | OCOPh | s (α) | H (β) | CH₃ | O-ribose (β) | O-ribose (β) | CO₂H | 2 |
| 45 | OCOPh | s (α) | H (α) | CH₃ | O-ribose (α) | O-ribose (α) | CO₂Me | 2 |
| 46 | COCPh | s (α) | H (α) | CH₃ | O-ribose (β) | O-ribose (β) | CO₂Me | 2 |
| 47 | OCOPh | s (α) | H (β) | CH₃ | O-ribose (α) | O-ribose (α) | CO₂Me | 2 |
| 48 | OCOPh | s (α) | H (β) | CH₃ | O-ribose (β) | O-ribose (β) | CO₂Me | 2 |
| 49 | O‖OCOEt | s (α) | H (β) | CH₃ | O-glucose (α) | O-glucose (β) | CO₂Me | 2 |
| 50 | O‖OCOEt | s (α) | H (β) | CH₃ | O-glucose (β) | O-glucose (α) | CO₂Me | 2 |
| 51 | O‖OCOEt | s (α) | H (α) | CH₃ | O-glucose (α) | O-glucose (β) | CO₂Me | 2 |
| 52 | O‖OCOEt | s (α) | H (α) | CH₃ | O-glucose (β) | O-glucose (α) | CO₂Me | 2 |

*s = single bond
d = double bond
α = below the plane of the ring
β = above the plane of the ring
**α =

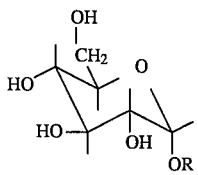

An α-glucoside
β =

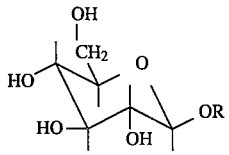

An β-glucoside
Mass Spectra
c m/e = 851
d m/e = 771
h m/e = 881
i m/e = 851

TABLE I-continued

| EX | A | a* | R¹* | R² | R³** | R⁴** | R⁵ | n |
|---|---|---|---|---|---|---|---|---| j m/e = 771
k m/e = 851
l m/e = 771
¹H NMR
b: (CDCl₃, 500MH$_z$) δ: 5.04(m, 1H, anomeric β — _H), 4.82(m, 1H, anomeric β — _H) +L6 e: (CDCl₃, 500MH$_z$) δ: 5.04(m, 1H, anomeric β — _H), 4.82(m, 1H, anomeric β — _H) f: (CDCl₃, 500MH$_z$) δ: 5.056(m, 1H, anomeric β — _H), 5.0414(m, 1H, anomeric β — _H) g: (CDCl₃, 500MH$_z$) δ: 5.0525(d, J = 3.96H$_z$, 1H, anomeric β — _H), 4.860(d, J = 3.96Hz, 1H, anomeric β — _H)

DOSAGE FORMS

The compounds of this invention can be administered to treat chronic viral infections such as AIDS (Acquired Immune Deficiency Syndrome) or herpes simplex; autoimmune diseases such as lupus, rheumatoid arthritis; diabetes, cystic fibrosis, growth hormone deficiencies; and cancer by any means that produces contact of the active agents with the appropriate site of action in a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms, by inhalation in the form of a nasal spray or lung inhaler, or topically as an ointment, cream or lotion.

Gelatin capsules contain the active ingredient and powdered carriers, such as lactose, sucrose mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

Suitable pharmaceutical carriers are described in *Remington's pharmaceutical Sciences*, A. Osol, a standard reference text in this field.

Useful pharmaceutical dosage forms for administration of the compounds of this invention can be illustrated as follows:

Capsules

A large number of unit capsules are prepared by filing standard two-piece hard gelatin capsules each with 50 milligrams of powdered active ingredient, 175 milligrams of lactose, 24 milligrams of talc, and 6 milligrams of magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 225 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by commonly used techniques.

Suspension

An aqueous suspension is prepared for oral administration so that each 5 milliliters contain 25 milligrams of sodium carboxymethyl cellulose, 5 milligrams of sodium benzoate, 1.0 grams of sorbitol solution, U.S.P., and 0.025 milliliters of vanillin.

Nasal Spray

An aqueous solution is prepared such that each 1 milliliter contains 10 milligrams of active ingredient, 1.8 milligrams methylparaben, 0.2 milligrams propylparaben and 10 milligrams methylcellulose. The solution is dispersed into milliliter vials.

Lung Inhaler

A homogenous mixture of the active ingredient in polysorbate 80 is prepared such that the final concentration of the active ingredient will be 10 milligrams per container and the final concentration of polysorbate 80 in the container will be 1% by weight. The mixture is dispensed into each can, the valves are crimped onto the can and the required amount of dichlorotetrafluoroethane is added under pressure.

Topical Formulation

An ointment for topical administration may be prepared by adding the active ingredient to a mixture of 48% by weight white petrolatum, 10% liquid petrolatum, 8% glycerol monostearate, 3% isopropyl myristate and 20% lanolin at 70° C. After thorough mixing, a warm solution of methyl and propyl parabens in water containing sodium acetone bisulfite is added such that the final concentrations of each paraben is 0.15%, of water is 8% and of sodium acetone bisulfite is 0.5%. The mixture is stirred until it has reached room temperature.

Use

The compounds of the invention have been shown to permeabilize biological membranes. This utility was demonstrated using an assay (Hoyt, D. W., et al. *Biochemistry*, Vol. 30, 10155 (1991)) in which a fluorescein derivative is encapsulated at self-quenching concentrations inside vesicles. An increase in fluorescent intensity upon addition of a test compound indicates leakage of the fluorescein derivative out of the vesicle and therefore implies a disruption of the membrane. The compounds of the present invention induce a rapid and significant increase in fluorescent intensity at very low concentrations (0.05 mM–0.5 mM).

A variation of the above assay (V. E. Carmichael et al. *J. Amer. Chem. Soc.*, Vol. III, 767 (1989)) was employed to determine whether the compounds make the membranes permeable to protons at extremely low concentrations (0.01 mM–0.005 mM). For this assay, the fluorescein derivative is encapsulated inside vesicles at non-quenching concentrations in a ph 6.5 buffer. The vesicles are diluted into a pH 5.5 buffer and a compound of formula (I) is added at a concentration lower than the concentration required to make the membranes permeable to the fluorescein derivative. After addition of compounds of the formula (I), the fluorescent intensity decreases, indicating that the membrane has become permeable to protons.

ASSAY I: Leakage of Carboxyfluorescein from Vesicles

To a 25 mL round bottom flask 20.5 mg egg yolk (Sigma, average MW 770.4) dissolved in $CHCl_3$/MeOH, 5.0 mg phosphatidyl glycerol (Sigma, MW 772) dissolved in $CHCl_3$/MeOH, and 12.7 mg repurified cholesterol (Aldrich, MW 386.66) were added. The molar ratio of egg yolk; phosphatidyl glycerol:cholesterol was 4:1:5 (66 µmoles total lipid). The solvent was removed on a rotary evaporator. The dried lipid mixture was then put under argon and 3 mL freshly distilled diethyl ether was added. After the lipid had redissolved, 1 mL of carboxyfluorescein dissolved in water (pH adjusted to 7.4) was added to a concentration of 180 mM (the concentration of carboxyfluorescein was determined by UV; the extinction coefficient at pH 7.4 is $5.6 \times 10^4$; $\lambda max = 492$). The lipid mixture containing carboxyfluorescein was sonicated under argon in a bath type sonicator at 5°–15° C. for 15–30 minutes. The mixture was then placed on the rotary evaporator and the organic solvent was removed. To separate the carboxyfluorescein-loaded vesicles from unencapsulated carboxyfluorescein, the remaining aqueous vesicle mixture was loaded on a sephadex G-25 column equilibrated with 145 mM NaCl/10 mM Hepes at pH 7.4. The carboxyfluorescein-loaded vesicles eluted in the first fraction after the void volume while the unencapsulated carboxyfluorescein remained on the column. The purified vesicles were diluted with 145 mM NaCl/10 mM Hepes buffer (pH 7.4) until the fluorescent intensity of the vesicle mixture measured approximately 10.

Because the carboxyfluorescein is encapsulated at self-quenching concentrations in the vesicles, an increase in fluorescent intensity over time indicates that the fluorophore is leaking out of the vesicles into the buffer. 5% Triton X100 was added in 50 uL MeOH to a sample of the vesicle solution to determine the maximum possible fluorescent increase (Triton X100 is a nonionic detergent that at the high concentration used breaks vesicles by solubilizing the lipids). The ability of each glycosylated steroid to induce the release of carboxyfluorescein from the vesicles was determined by monitoring the increase in fluorescent intensity upon addition of glycosteroid. For each experiment, 50 µL of glycosteroid in methanol (initial concentrations ranged from 0.6145 to 2.458 mM) was added to the cuvette and the fluorescent intensity followed over 10 minutes. A control in which 50 uL pure methanol was added showed that methanol alone does not cause a significant increase in fluorescent intensity. However, several of the glycosteroids efficiently permeabilized vesicle membranes at very low concentrations, permitting the carboxyfluorescein to leak out into the buffer. The results are summarized in Table II.

TABLE II

| EX | CONCENTRATION (mM)* | % increase in Fluorescence |
|---|---|---|
| Cholic Acid | 0.117 | 0 |
|  | 2.341 | 59.1 |
| Methyl Cholate | 0.117 | 25.4 |
| Chenodeoxycholic acid | 0.117 | 17.7 |
|  | 1.17 | 80.9 |
| Triton-X 100 | 4.04 | 100 |

TABLE II-continued

| EX | CONCENTRATION (mM)* | % increase in Fluorescence |
|---|---|---|
|  | 1.17 | 46.4 |
|  | 0.117 | 18.6 |
| Deoxycholic Acid | 0.117 | 0 |
|  | 1.17 | 82.7 |
| 1 | 0.117 | 0 |
| 2 | 0.117 | 10 |
| 3 | 2.34 | 0 |
| 4 | 0.117 | 0 |
| 5 | 0.117 | 57.3 |
| 7 | 0.117 | 89.1 |
| 8 | 0.117 | 89.1 |
| 9 | 0.117 | 24.5 |
| 10 | 0.117 | 0 |
| 11 | 0.117 | 98 |
| 13 | 0.117 | 0 |

*Final concentration after dilution.

ASSAY II: Proton Transport across Lipid Membranes

This assay was used to judge the ability of protons to pass across vesicle membranes treated with glycosteroids. Vesicles loaded with carboxyfluorescein at non-self-quenching concentrations were prepared exactly as described above except that the carboxyfluorescein was added to the lipid mixture in 1 mL water (pH 6.5) at a concentration of 1 mM. After sonication under argon and rotary evaporation to remove the diethyl ether, the carboxyfluorescein-loaded vesicles were purified on a sephadex-G25 column as described above. The concentration of the vesicle solution after purification on the G-25 column was adjusted until the fluorescent intensity equaled 100 after 100-fold dilution into 80 mM NaCl/5 mM Hepes buffer at pH 5.5.

A 100-fold dilution of the vesicle stock into pH 5.5 buffer was made immediately before each experiment and 1 mL of the diluted solution was put in a cuvette. To evaluate the ability of the glycosteroids to facilitate transport of protons across the lipid bilayer, 50 µL of a 0.245M solution of each glycosteroid in methanol was added to the 1 mL vesicle solution in a fluorescence cuvette and the change in fluorescent intensity was monitored over a period of 10 minutes. A significant decrease in fluorescence indicates that the glycosteroid in question facilitates the transport of protons across the membrane. This assay is based on the fact that the fluorescent intensity of carboxyfluorescein is much greater at pH 6.5 than at pH 5.5. If vesicles prepared at pH 6.5 are diluted into a buffer at pH 5.5, the fluorescent intensity will drop over time as the pH gradient across the membrane collapses. As a control, 50 µL pure MeOH was added and the fluorescent intensity was found not to change significantly. Addition of MeOH at low concentrations therefore does not make the vesicles permeable to protons. The results are summarized in Table III.

TABLE III

| EX | Concentration (mM)* | % Decrease in Fluorescence |
|---|---|---|
| Triton-X 100 | 4.04 | 100 |
|  | 0.0116 | 2.43 |
| Gramicidin | 0.00579 | 87.2 |
|  | 0.000579 | 81.6 |
| Cholic Acid | 0.0116 | 1.0 |
| Methyl Cholate | 0.0116 | 5.4 |
| Chenodeoxycholic Acid | 0.0116 | 8.2 |
| Deoxycholic Acid | 0.0116 | 5.39 |
| 1 | 0.0116 | 7.6 |

TABLE III-continued

| EX | Concentration (mM)* | % Decrease in Fluorescence |
|---|---|---|
|  | 0.00579 | 4.3 |
| 2 | 0.0116 | 8.6 |
|  | 0.00579 | 1.7 |
| 3 | 0.0116 | 35.4 |
|  | 0.00579 | 21.0 |
| 4 | 0.0116 | 12.3 |
|  | 0.00579 | 7.89 |
| 5 | 0.0116 | 26.1 |
|  | 0.00579 | 19.4 |
| 7 | 0.0116 | 19.8 |
|  | 0.00579 | 15.2 |
| 8 | 0.0116 | 32.2 |
|  | 0.00579 | 20.6 |
| 9 | 0.0116 | 43.0 |
|  | 0.00579 | 27.4 |
| 11 | 0.0116 | 22.0 |
|  | 0.00585 | 14.7 |
| 13 | 0.0116 | 70.6 |
|  | 0.00579 | 35.2 |
|  | 0.000579 | 2.8 |

*Final concentration after dilution.

What is claimed is:

1. A pharmaceutical composition comprising a suitable pharmaceutical carrier and an effective amount of a compound having the formula:

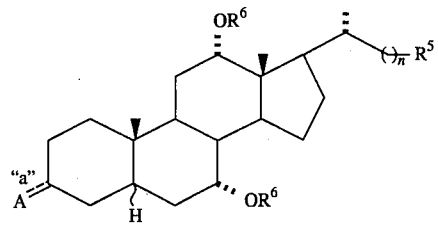

wherein

A is O, OH, $OR^6$, $NR^7R^8$, $N_3$, $NHCOR^7$, $OCOAr$, $O-CO-OR^9$, $OCOR^9$, $NHCH_2C_6H_5$, and in which Ar is phenyl or phenyl substituted with 1–3 groups selected from the group consisting of halogen, $C_1$–$C_{12}$ alkyl or $C_1$–$C_3$ alkoxy;

"a" is a single bond in the alpha or beta configuration with the proviso that when A=O, "a" is a double bond;

$R^5$ is $CO_2R^{10}$, $CH_2OR^9$, $CONH_2$, $CONHR^7$, $CONR^7R^8$, $CO-S-R^{10}$, $CH_2S(O)_p-S-R^{10}$, $CH_2NH_2$, $CH_2NHR^7$, $CH_2NR^7R^8$, $CH_2-SO(O)_p-S-R^{10}$;

$R^6$ is a glycosyl moiety comprising 1–10 monosaccharide units in which the glycosidic linkage at the anomeric carbon of each monosaccharide unit is independently alpha or beta;

$R^7$ and $R^8$, independently are H, $C_1$–$C_4$ alkyl, $C_3$–$C_7$ cycloalkyl, $C_4$–$C_{10}$ alkylcycloalkyl, phenyl, benzyl, or, taken together are $(CH_2)_f$, where f=3–6;

$R^9$ is H, or $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

p is 0, 1 or 2;

n is 0, 1 or 2;

or a pharmaceutically suitable salt thereof.

2. The pharmaceutical composition of claim 1 in which A is OH, $OR^6$, $O-CO-OR^9$, $OCOC_6H_5$, $OCOC_6H_4-pOMe$ or $NH_2$.

3. The pharmaceutical composition of claim 1 in which "a" is a single bond.

4. The pharmaceutical composition of claim 1 in which said glycosyl moiety is a hexose selected from the group consisting of D-allose, D-altrose, D-glucose, D-mannose, D-gulose, D-idose, D-galactose, D-talose or a deoxy derivative thereof.

5. The pharmaceutical composition of claim 1 in which said glycosyl moiety is a furanose selected from the group consisting of D-ribose, D-arabinose, D-xylose, D-lyxose or a deoxy derivative thereof.

6. The pharmaceutical composition of claim 1 in which $R^5$ is $CO_2R^{10}$ or $CONR^7R^8$.

7. The pharmaceutical composition of claim 1 in which $R^6$ comprises a monosaccharide in which the glycosidic linkage at the anomeric carbon of said monosaccharide is alpha ($\alpha$).

8. The pharmaceutical composition of claim 1 in which $R^6$ comprises a monosaccharide in which the glycosidic linkage at the anomeric carbon of said monosaccharide is beta ($\beta$).

9. The pharmaceutical composition of claim 1 in which $R^{10}$ is H or $C_1$–$C_{10}$ alkyl.

10. The pharmaceutical composition of claim 7 in which said monosaccharide is 2,3,4,6-tetra-O-benzyl-D-glucose.

11. The pharmaceutical composition of claim 8 in which said monosaccharide is 2,3,4,6-tetra-O-benzyl-D-glucose.

12. The pharmaceutical composition of claim 7 in which said monosaccharide is D-glucose.

13. The pharmaceutical composition of claim 8 in which said monosaccharide is D-glucose.

14. The pharmaceutical composition of claim 1 in which

A is OH, $OR^6$, O—CO—$OR^9$, $OCOC_6H_5$, $OCOC_6H_4$—pOMe, $NH_2$;

"a" is a single bond;

$R^5$ is $CO_2R^{10}$, $CONR^7R^8$;

$R^6$ is a glycosyl moiety comprising a protected or deprotected hexose having an anomeric alpha or beta glycosidic linkage; and $R^{10}$ is H or $C_1$–$C_{10}$ alkyl.

15. A method of transporting a therapeutically significant compound across a biological membrane comprising contacting a biological membrane with a therapeutically significant compound in the presence of an effective amount of a second compound of the formula:

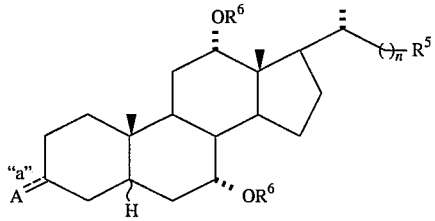

in which

A is O, OH, $OR^6$, $NR^7R^8$, $N_3$, $NHCOR^7$, OCOAr, O—CO—$OR^9$, $OCOR^9$, $NHCH_2C_{6H5}$, and in which Ar is phenyl or phenyl substituted with 1–3 groups selected from the group consisting of halogen, $C_1$–$C_{12}$alkyl or $C_1$–$C_3$ alkoxy;

"a" is a single bond in the alpha or beta configuration with the proviso that when A=O, "a" is a double bond;

$R^5$ is $CO_2R^{10}$, $CH_2OR^9$, $CONH_2$, $CONHR^7$, $CONR^7R^8$, CO—S—$R^{10}$, $CH_2S(O)_p$—S—$R^{10}$, $CH_2NH_2$, $CH_2NHR^7$, $CH_2NR^7R^8$, $CH_2$—$SO(O)_p$—S—$R^{10}$;

$R^6$ is a glycosyl moiety comprising 1–10 monosaccharide units in which the glycosidic linkage at the anomeric carbon of each monosaccharide unit is independently alpha or beta;

$R^7$ and $R^8$, independently are H, $C_1$–$C_4$ alkyl, $C_3$–$C_7$ cycloalkyl, $C_4$–$C_{10}$ alkylcycloalkyl, phenyl, benzyl, or, taken together are $(CH_2)_f$, where f=3–6;

$R^9$ is H, or $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

p is 0, 1 or 2;

n is 0, 1 or 2;

or a pharmaceutically suitable salt thereof.

16. The method of claim 15 in which A is OH, $OR^6$, O—CO—$OR^9$, $OCOC_6H_5$, $OCOC_6H_4$—pOMe or $NH_2$.

17. The method of claim 15 in which "a" is a single bond.

18. The method of claim 15 in which said glycosyl moiety is a hexose selected from the group consisting of D-allose, D-altrose, D-glucose, D-mannose, D-gulose, D-idose, D-galactose, D-talose or a deoxy derivative thereof.

19. The method of claim 15 in which said glycosyl moiety is a furanose selected from the group consisting of D-ribose, D-arabinose, D-xylose, D-lyxose or a deoxy derivative thereof.

20. The method of claim 15 in which $R^5$ is $CO_2R^{10}$ or $CONR^7R^8$.

21. The method of claim 15 in which $R^6$ comprises a monosaccharide in which the glycosidic linkage at the anomeric carbon of said monosaccharide is alpha ($\alpha$).

22. The method of claim 15 in which $R^6$ comprises a monosaccharide in which the glycosidic linkage at the anomeric carbon of said monosaccharide is beta ($\beta$).

23. The method of claim 15 in which the group $R^{10}$ is H or $C_{31}$–$C_{10}$ alkyl.

24. The method of claim 21 in which said monosaccharide is 2,3,4,6-tetra-O-benzyl-D-glucose.

25. The method of claim 22 in which said monosaccharide is 2,3,4,6-tetra-O-benzyl-D-glucose.

26. The method of claim 21 in which said monosaccharide is D-glucose.

27. The method of claim 22 in which said monosaccharide is D-glucose.

28. The method of claim 15 in which

A is OH, $OR^6$, $OCOC_6H_5$, $OCOC_6H_4$—pOMe, $NH_2$;

"a" is a single bond;

$R^5$ is $CO_2R^{10}$, $CONR^7R^8$;

$R^6$ is a glycosyl moiety comprising a protected or deprotected hexose having an anomeric alpha or beta glycosidic linkage; and $R^{10}$ is H or $C_1$–$C_{10}$ alkyl.

29. A pharmaceutical composition comprising:

a) an effective amount of a compound of the formula:

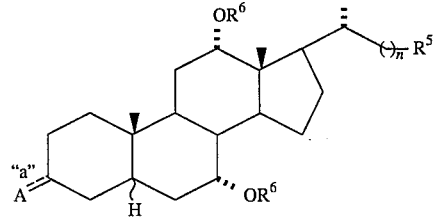

in which

A is O, OH, $OR^6$, $NR^7R^8$, $N_3$, $NHCOR^7$, OCOAr,

O—CO—OR⁹, OCOR⁹, NHCH₂C₆H₅, and in which Ar is phenyl or phenyl substituted with 1–3 groups selected from the group consisting of halogen, $C_1$–$C_{12}$alkyl or $C_1$–$C_3$ alkoxy;

"a" is a single bond in the alpha or beta configuration with the proviso that when A=O, "a" is a double bond;

$R^5$ is $CO_2R^{10}$, $CH_2OR^9$, $CONH_2$, $CONHR^7$, $CONR^7R^8$, CO—S—$R^{10}$, $CH_2S(O)_p$—S—$R^{10}$, $CH_2NH_2$, $CH_2NHR^7$, $CH_2NR^7R^8$, $CH_2$—SO(O)$_p$—S—$R^{10}$;

$R^6$ is a glycosyl moiety comprising 1–10 monosaccharide units in which the glycosidic linkage at the anomeric carbon of each monosaccharide unit is independently alpha or beta;

$R^7$ and $R^8$, independently are H, $C_1$–$C_4$ alkyl, $C_3$–$C_7$ cycloalkyl, $C_4$–$C_{10}$ alkylcycloalkyl, phenyl, benzyl, or, taken together are $(CH_2)_f$, where f=3–6;

$R^9$ is H, or $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

p is 0, 1 or 2;

n is 0, 1 or 2;

or a pharmaceutically suitable salt thereof;

b) an effective amount of a therapeutically significant compound; and c) a pharmaceutically acceptable carrier.

30. The pharmaceutical composition of claim 29 in which the compound of the formula and said therapeutically significant compound are present as an admixture.

31. The pharmaceutical composition of claim 29 in which the compound of the formula and said therapeutically significant compound are present as a conjugate.

32. The pharmaceutical composition of claim 1 in which the compound of the formula is not 3α-ethylcarbonate-cis-5,10-bis-α,α-7,12-(2,3,4,6-tetra-O-benzyl)glucosyl cholic acid.

33. The pharmaceutical composition of claim 29 in which the compound of the formula is not 3α-ethylcarbonate-cis-5,10-bis-α,α-7,12-(2,3,4,6-tetra-O-benzyl)glucosyl cholic acid.

34. The pharmaceutical composition of claim 33 in which A is OH, $OR^6$, O—CO—$OR^9$, $OCOC_6H_5$, $OCOC_6H_4$—pOMe or $NH_2$.

35. The pharmaceutical composition of claim 33 in which "a" is a single bond.

36. The pharmaceutical composition of claim 33 in which said glycosyl moiety is a hexose selected from the group consisting of D-allose, D-altrose, D-glucose, D-mannose, D-gulose, D-idose, D-galactose, D-talose or a deoxy derivative thereof.

37. The pharmaceutical composition of claim 33 in which said glycosyl moiety is a furanose selected from the group consisting of D-ribose, D-arabinose, D-xylose, D-lyxose or a deoxy derivative thereof.

38. The pharmaceutical composition of claim 33 in which $R^5$ is $CO_2R^{10}$ or $CONR^7R^8$.

39. The pharmaceutical composition of claim 33 in which $R^6$ comprises a monosaccharide in which the glycosidic linkage at the anomeric carbon of said monosaccharide is alpha (α).

40. The pharmaceutical composition of claim 33 in which $R^6$ comprises a monosaccharide in which the glycosidic linkage at the anomeric carbon of said monosaccharide is beta (β).

41. The pharmaceutical composition of claim 33 in which $R^{10}$ is H or $C_1$–$C_{10}$ alkyl.

42. The pharmaceutical composition of claim 39 in which said monosaccharide is 2,3,4,6-tetra-O-benzyl-D-glucose.

43. The pharmaceutical composition of claim 40 in which said monosaccharide is 2,3,4,6-tetra-O-benzyl-D-glucose.

44. The pharmaceutical composition of claim 39 in which said monosaccharide is D-glucose.

45. The pharmaceutical composition of claim 40 in which said monosaccharide is D-glucose.

46. The pharmaceutical composition of claim 33 in which A is OH, $OR^6$, O—CO—$OR^9$, $OCOC_6H_5$, $OCOC_6H_4$—pOMe, $NH_2$;

"a" is a single bond;

$R^5$ is $CO_2R^{10}$, $CONR^7R^8$;

$R^6$ is D-glucose, which is optionally protected with benzyl or pivaloyl groups, where the glycosidic linkage at the anomeric carbon atom is alpha or beta; and $R^{10}$ is H or $C_1$–$C_{10}$ alkyl.

47. The pharmaceutical composition of claim 29 in which the compound of the formula is 3α-O-benzoyl-trans-5,10-bis-β,β-7,12-glucosyl cholic acid methyl ester.

48. The pharmaceutical composition of claim 29 in which the compound of the formula is 3α-hydroxy-cis-5,10-bis-α,α-7,12-glucosyl cholic acid.

49. The pharmaceutical composition of claim 29 in which the compound of the formula is 3α-hydroxy-cis-5,10-bis-α,α-7,12-glucosyl cholic acid methyl ester.

50. The pharmaceutical composition of claim 29 in which the compound of the formula is 3α-hydroxy-cis-5,10-bis-α,α-7,12-glucosyl-25-tryptophanyl cholic acid.

51. The pharmaceutical composition of claim 29 in which the compound of the formula is 3α-ethylcarbonate-cis-5,10-bis-α,α-7,12-glucosyl cholic acid methyl ester.

52. The pharmaceutical composition of claim 29 in which the compound of the formula is 3α-ethylcarbonate-trans-5,10-bis-α,α-7,12-glucosyl cholic acid methyl ester.

53. The pharmaceutical composition of claim 29 in which the compound of the formula is 3α-O-benzoyl-cis-5,10-bis-α,α-7,12-glucosyl cholic acid methyl ester.

54. The pharmaceutical composition of claim 29 in which the compound of the formula is 3α-O-p-methoxybenzoyl-cis-5,10-bis-α,α-7,12-glucosyl cholic acid methyl ester.

55. The pharmaceutical composition of claim 29 in which the compound of the formula is 3α-O-benzoyl-cis-5,10-bis-β,β-7,12-glucosyl cholic acid methyl ester.

56. The pharmaceutical composition of claim 29 in which the compound of the formula is 3α-hydroxy-cis-5,10-bis-β,β-7,12-glucosyl cholic acid.

57. The pharmaceutical composition of claim 29 in which the compound of the formula is 3α-O-benzoyl-trans-5,10-bis-α,α-7,12-glucosyl cholic acid methyl ester.

58. The pharmaceutical composition of claim 29 in which the compound of the formula is 3α-hydroxy-trans-5,10-bis-β,β-7,12 glucosyl cholic acid.

59. The pharmaceutical composition of claim 36 in which said hexose or deoxy derivative thereof is protected with a protecting group selected from the group consisting of benzyl, pivaloyl, trimethylsilyl, tert-butyldimethylsilyl, tert-butyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl or allyl.

60. The pharmaceutical composition of claim 37 in which said furanose or deoxy derivative thereof is protected with a protecting group selected from the group consisting of benzyl, pivaloyl, trimethylsilyl, tert-butyldimethylsilyl, tert-butyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl or allyl.

61. The pharmaceutical composition of claim 29 which is in the form of a capsule, powder or tablet.

62. The pharmaceutical composition of claim 29 which is injectable.

63. The pharmaceutical composition of claim 29 which is in the form of a suspension.

64. The pharmaceutical composition of claim 29 which is in the form of a nasal spray or lung inhaler.

65. The pharmaceutical composition of claim 29 which is in the form of a topical formulation.

66. The method of claim 15 in which said second compound is present at a concentration of about 0.005 mM to about 0.5 mM.

67. The method of claim 66 in which said second compound is present at a concentration of about 0.005 mM to about 0.01 mM.

68. The method of claim 15 in which said second compound is present at a concentration of about 0.05 mM to about 0.5 mM.

69. The method of claim 15 in which said biological membrane is contacted with said therapeutically significant compound by admixing said therapeutically significant compound with said second compound.

70. The method of claim 15 in which said biological membrane is contacted with said therapeutically significant compound by conjugating said therapeutically significant compound to said second compound.

71. The method of claim 15 in which said biological membrane is in a mammal.

72. The method of claim 18 in which said hexose or deoxy derivative thereof is protected with a protecting group selected from the group consisting of benzyl, pivaloyl, trimethylsilyl, tert-butyldimethylsilyl, tert-butyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl or allyl.

73. The method of claim 15 in which said furanose or deoxy derivative thereof is protected with a protecting group selected from the group consisting of benzyl, pivaloyl, trimethylsilyl, tert-butyldimethylsilyl, tert-butyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl or allyl.

* * * * *